United States Patent
Minoda et al.

(10) Patent No.: US 11,208,367 B2
(45) Date of Patent: Dec. 28, 2021

(54) PRODUCTION METHOD FOR P-XYLENE

(71) Applicant: ENEOS Corporation, Tokyo (JP)

(72) Inventors: Ai Minoda, Tokyo (JP); Masanari Akiyama, Tokyo (JP); Yasuhiro Araki, Tokyo (JP)

(73) Assignee: ENEOS CORPORATION, Tokyo (JP)

( * ) Notice: Subject to any disclaimer, the term of this patent is extended or adjusted under 35 U.S.C. 154(b) by 0 days.

(21) Appl. No.: 17/042,536

(22) PCT Filed: Mar. 19, 2019

(86) PCT No.: PCT/JP2019/011520
§ 371 (c)(1),
(2) Date: Sep. 28, 2020

(87) PCT Pub. No.: WO2019/188602
PCT Pub. Date: Oct. 3, 2019

(65) Prior Publication Data
US 2021/0009487 A1 Jan. 14, 2021

(30) Foreign Application Priority Data
Mar. 30, 2018 (JP) .............................. JP2018-067599

(51) Int. Cl.
*C07C 5/41* (2006.01)
*C07C 2/52* (2006.01)
*C07C 15/08* (2006.01)

(52) U.S. Cl.
CPC ................ *C07C 5/41* (2013.01); *C07C 2/52* (2013.01); *C07C 15/08* (2013.01)

(58) Field of Classification Search
CPC .. C07C 5/41; C07C 5/417; C07C 2/28; C07C 2/52; C07C 15/08; C07C 2523/62; C07C 2531/10; B01J 23/42; B01J 23/626; B01J 21/04; Y02P 20/52; C07B 61/00
See application file for complete search history.

(56) References Cited

U.S. PATENT DOCUMENTS

2011/0087000 A1* 4/2011 Peters ................ C07C 5/415
528/308.3

FOREIGN PATENT DOCUMENTS

| | | |
|---|---|---|
| GB | 1598809 | 9/1981 |
| JP | 2011-079815 | 4/2011 |
| JP | 2015-193647 | 11/2015 |
| WO | 2017/179708 | 10/2017 |
| WO | 2018/092840 | 5/2018 |
| WO | 2018/193668 | 10/2018 |

OTHER PUBLICATIONS

ISR issued in WIPO Patent Application No. PCT/JP2019/011520, dated May 21, 2019, English translation.
Written Opinion issued in WIPO Patent Application No. PCT/JP2019/011520, dated May 21, 2019, English translation.
IPRP issued in WIPO Patent Application No. PCT/JP2019/011520, dated Oct. 6, 2020, English translation.

* cited by examiner

*Primary Examiner* — Youngsul Jeong
*Assistant Examiner* — Jason Y Chong
(74) *Attorney, Agent, or Firm* — Ieenblum & Bernstein, P.L.C.

(57) ABSTRACT

A method for producing p-xylene, comprising: a dimerization step of bringing a first raw material comprising isobutene into contact with a dimerization catalyst to generate C8 components comprising diisobutylene; a cyclization step of bringing a second raw material comprising the C8 components into contact with a dehydrogenation catalyst comprising Pt in the presence of water to obtain a reaction product comprising p-xylene; and a collection step of collecting p-xylene from the reaction product.

7 Claims, No Drawings

PRODUCTION METHOD FOR P-XYLENE

TECHNICAL FIELD

The present invention relates to a method for producing p-xylene.

BACKGROUND ART p-Xylene is an industrially useful substance as a raw material of terephthalic acid, which is an intermediate raw material of polyester fiber or PET resin. As a method for producing p-xylene, for example, a method for producing p-xylene from raw material containing ethylene (Patent Literature 1) and a method for producing p-xylene from biomass (Patent Literature 2) are known, and various methods for efficiently producing p-xylene have been examined.

CITATION LIST

Patent Literature

Patent Literature 1: Japanese Unexamined Patent Publication No. 2011-79815
Patent Literature 2: Japanese Unexamined Patent Publication No. 2015-193647

SUMMARY OF INVENTION

Technical Problem

An object of the present invention is to provide a method for producing p-xylene which enables to obtain p-xylene from C4 components containing isobutene as a raw material at a high process efficiency.

Solution to Problem

One aspect of the present invention relates to a method for producing p-xylene, comprising: a dimerization step of bringing a first raw material comprising isobutene into contact with a dimerization catalyst to generate C8 components comprising diisobutylene; a cyclization step of bringing a second raw material comprising the above-mentioned C8 components into contact with a dehydrogenation catalyst comprising Pt in the presence of water to obtain a reaction product comprising p-xylene; and a collection step of collecting p-xylene from the reaction product.

In the above-mentioned production method, in the cyclization step, a cyclodehydrogenation reaction is performed in the presence of water using a specific dehydrogenation catalyst. By this, the monomerization of the C8 components to the C4 components can be inhibited in the above-mentioned production method while a good collection rate of p-xylene is maintained.

In the cyclization step, the monomerization of the C8 components to the C4 components occurs as side reaction besides the cyclodehydrogenation reaction. For this reason, the C8 components other than p-xylene (for example, an unreacted fraction) and the C4 components (for example, isobutene and isobutane) produced by the monomerization are contained in the reaction product, besides p-xylene. Although the recycle of the C8 components for the cyclization step enables to contribute to the production of p-xylene, the C4 components need to be recycled by returning the C4 components to the dimerization step. In the above-mentioned production method, inhibiting the monomerization of the C8 components increases the proportion of the C8 components to components other than p-xylene in the reaction product (namely, the proportion of components which are more suitable for recycle) and enables to obtain p-xylene at a high process efficiency.

In a production method according to one aspect, in the above-mentioned collection step, a C8 collected fraction comprising at least one selected from the group consisting of diisobutylene, 2,2,4-trimethylpentane, 2,5-dimethylhexane, 2,5-dimethylhexene and 2,5-dimethylhexadiene may be further collected from the above-mentioned reaction product.

In a production method according to one aspect, the above-mentioned C8 collected fraction may be recycled as the above-mentioned second raw material of the above-mentioned cyclization step.

In a production method according to one aspect, in the above-mentioned collection step, a C4 collected fraction comprising at least one selected from the group consisting of isobutene and isobutane may be further collected from the above-mentioned reaction product.

In a production method according to one aspect, the above-mentioned C4 collected fraction may be recycled as the above-mentioned first raw material of the above-mentioned dimerization step.

In one aspect, the above-mentioned dimerization catalyst may comprise at least one acidic catalyst selected from the group consisting of sulfuric acid, zeolite, solid phosphoric acid, hydrofluoric acid, ionic liquids, and ion-exchange resins.

In one aspect, the above-mentioned dehydrogenation catalyst may further comprise Sn.

Advantageous Effects of Invention

According to the present invention, a method for producing p-xylene from C4 components containing isobutene as a raw material, wherein the method enables to obtain p-xylene at a high process efficiency is provided.

DESCRIPTION OF EMBODIMENTS

Preferred embodiments of the present invention will be described hereinafter. However, the present invention is not limited to the following embodiments in any way.

A method for producing p-xylene according to the present embodiment comprises: a dimerization step of bringing a first raw material comprising isobutene into contact with a dimerization catalyst to generate C8 components comprising diisobutylene; a cyclization step of bringing a second raw material comprising the above-mentioned C8 components into contact with a dehydrogenation catalyst comprising Pt in the presence of water to obtain a reaction product comprising p-xylene; and a collection step of collecting p-xylene from the above-mentioned reaction product.

Diisobutylene herein refers to 2,4,4-trimethyl-1-pentene, 2,4,4-trimethyl-2-pentene or a mixture thereof.

In the production method according to the present embodiment, by performing a cyclodehydrogenation reaction using a specific dehydrogenation catalyst in the presence of water in the cyclization step, the monomerization of the C8 components to the C4 components can be inhibited while a good collection rate of p-xylene is maintained. That is, in the production method according to the present embodiment, the proportion of the C4 components in the reaction product obtained in the cyclization step decreases, and the proportion of the C8 components increases. While the C4 components need to be recycled by returning the C4 components to the dimerization step, the C8 components can easily contribute to the production of p-xylene as being recycled for cyclization step. According to the production method according to the present embodiment, therefore, inhibiting the monomerization of the C8 components thus increases the proportion of the C8 components to components other than p-xylene in the reaction product (namely, the proportion of components which are more suitable for recycle) and enables to obtain p-xylene at a high process efficiency.

The steps of the production method according to the present embodiment will be described in detail hereinafter.

(Dimerization Step)

A dimerization step is a step of bringing a first raw material containing isobutene into contact with a dimerization catalyst using the isobutene as a raw material component to obtain C8 components containing diisobutylene. The first raw material may be provided to the dimerization reaction in the form of gas.

In the dimerization step, the first raw material may further contain C4 components other than isobutene, namely hydrocarbons having 4 carbon atoms other than isobutene. Examples of the hydrocarbons having 4 carbon atoms other than isobutene include isobutane, normal butene and normal butane.

As a C4 component other than isobutene in the first raw material, isobutane is preferable. Since isobutane can be converted into isobutene in the below-mentioned cyclization step, isobutane can contribute to improvement in the yield of p-xylene.

In one preferred aspect, the first raw material contains isobutene and isobutane. At this time, the ratio of the total content of isobutene and isobutane to the C4 components in the first raw material may be, for example, 5% by mass or more, and is preferably 10% by mass or more, and more preferably 30% by mass or more. The upper limit of the ratio of the total content of isobutene and isobutane to the C4 components in the first raw material is not particularly limited, may be, for example, 100% by mass, and may be 80% by mass or less.

In the dimerization step, a C4 collected fraction collected in the below-mentioned collection step may be recycled as some or all of the first raw material.

The first raw material may further contain a component other than hydrocarbons. The first raw materials may further contain, for example, an inert gas as a diluent. Examples of the inert gas include nitrogen. The first raw material may further contain other gases such as carbon dioxide.

The isobutene concentration in the first raw material may be, for example, 1% by mass or more, and may be 5% by mass or more. The upper limit of the isobutene concentration in the first raw material is not particularly limited, and, for example, may be 100% by mass.

The dimerization catalyst may be a catalyst having activity for the dimerization reaction of isobutene. Example of the dimerization catalyst include acidic catalysts such as sulfuric acid, zeolite, solid phosphoric acid, ion-exchange resins, hydrofluoric acid and ionic liquids.

In the dimerization step, the reaction conditions of dimerization reaction are not particularly limited, and may be optionally changed depending on the activity of a catalyst to be used and the like.

The C8 components containing diisobutylene are generated in the dimerization step. The C8 components are hydrocarbons having 8 carbon atoms, and the hydrocarbons are generated by reacting two molecules of hydrocarbons having 4 carbon atoms (isobutene, isobutane, and the like) in the first raw material. The C8 components may contain, for example, a dimer of isobutene, a reaction product of isobutene and isobutane, and the like. The C8 components may further contain at least one selected from the group consisting of, for example, 2,2,4-trimethylpentane, 2,5-dimethylhexane, 2,5-dimethylhexene, and 2,5-dimethylhexadiene besides isobutylene.

In a dimerization step, the first product containing the C8 components is obtained from the first raw material. In the present embodiment, the first product may be used as a raw material of the below-mentioned cyclization step as it is.

(Cyclization Step)

In a cyclization step, a second raw material containing the C8 components is brought into contact with a dehydrogenation catalyst in the presence of water to obtain p-xylene which is a product of the cyclodehydrogenation reaction of the C8 components. The second raw material may be provided to the cyclodehydrogenation reaction in the form of gas.

In the cyclization step, the first product obtained in the dimerization step may be used as the second raw material as it is. That is, the second raw material may contain the first product, and may further contain hydrocarbons other than the C8 components (for example, C4 components such as isobutene, isobutane, normal butene and normal butane).

In the cyclization step, a C8 collected fraction collected in the below-mentioned collection step may be recycled as some of the second raw material.

The second raw material may further contain a component other than hydrocarbons. The second raw materials may further contain, for example, an inert gas as a diluent. Examples of the inert gas include nitrogen. The second raw material gas may further contain other gas such as hydrogen and carbon dioxide.

The C8 components are hydrocarbons having 8 carbon atoms. It is desirable that the C8 components contain a p-xylene precursor selected from the group consisting of isobutylene, 2,2,4-trimethylpentane, 2,5-dimethylhexane, 2,5-dimethylhexene, and 2,5-dimethylhexadiene. For example, it is preferable that the proportion of the above-mentioned p-xylene precursor to the C8 components be 50% by mass or more, it is more preferable that the proportion be 80% by mass or more, and it is further preferable that the proportion be 95% by mass or more.

The dehydrogenation catalyst in the present embodiment will be described in detail hereinafter.

The dehydrogenation catalyst is a catalyst containing Pt. The dehydrogenation catalyst may further contain a Group 14 metal element. Here, the Group 14 metal element means a metal element belonging to Group 14 of the periodic table in the long-form periodic table of elements based on the convention of IUPAC (International Union of Pure and Applied Chemistry). The Group 14 metal element may be at least one selected from the group consisting of, for example, germanium (Ge), tin (Sn) and lead (Pb). Among these, Sn is preferable from the viewpoint of improvement in activity.

The dehydrogenation catalyst may have, for example, a carrier and an active metal supported on the carrier. In this case, the dehydrogenation catalyst has Pt as an active metal. The dehydrogenation catalyst may further have a Group 14 metal element as an active metal.

As the carrier, an inorganic carrier is preferable, and an inorganic oxide carrier is more preferable. It is preferable that the carrier contain at least one element selected from the group consisting of Al, Mg, Si, Zr, Ti and Ce, and it is more preferable that the carrier contain at least one element selected from the group consisting of Al, Mg and Si. As the carrier, an inorganic oxide carrier containing Al and Mg is used particularly suitably from the viewpoints that side reactions are inhibited, and p-xylene is obtained more efficiently.

One preferred aspect of the dehydrogenation catalyst will be shown below.

The dehydrogenation catalyst of the present aspect (hereinafter also referred to as a first dehydrogenation catalyst) is a catalyst in which a supported metal including Pt and Sn is supported on a carrier containing Al and a Group 2 metal element. Here, the Group 2 metal element means a metal element belonging to Group 2 of the periodic table in the long-form periodic table of elements based on the convention of IUPAC (International Union of Pure and Applied Chemistry).

The Group 2 metal element may be at least one selected from the group consisting of, for example, beryllium (Be), magnesium (Mg), calcium (Ca), strontium (Sr) and barium (Ba). Among these, it is preferable that the Group 2 metal element be Mg.

In the dehydrogenation catalyst of the present aspect, the content of Al may be 15% by mass or more, or may be 25% by mass or more, based on the total mass of the dehydrogenation catalyst. The content of Al may be 40% by mass or less.

In the dehydrogenation catalyst of the present aspect, it is preferable that the content of the Group 2 metal element be 10% by mass or more, and it is more preferable that the content be 13% by mass or more, based on the total mass of the dehydrogenation catalyst. It is preferable that the content of the Group 2 metal element be 20% by mass or less, and it is more preferable that the content be 16% by mass or less, based on the total mass of the dehydrogenation catalyst.

In the dehydrogenation catalyst of the present aspect, it is preferable that the content of Pt be 0.1% by mass or more, and it is more preferable that the content be 0.5% by mass or more based on the total mass of the dehydrogenation catalyst. It is preferable that the content of Pt be 5% by mass or less, and it is more preferable that the content be 3% by mass or less based on the total mass of the dehydrogenation catalyst. When the content of Pt is 0.1% by mass or more, the amount of platinum per the amount of the catalyst increases, and the reactor size can be reduced. When the content of Pt is 5% by mass or less, Pt particles formed on the catalyst have a suitable size for dehydrogenation reaction, and the platinum surface area per unit platinum weight increases, and thus a more efficient reaction system can therefore be achieved.

In the dehydrogenation catalyst of the present aspect, it is preferable that the content of Sn be 2% by mass or more, and it is more preferable that the content be 4% by mass or more based on the total mass of the dehydrogenation catalyst. It is preferable that the content of Sn be 9% by mass or less, and it is more preferable that the content be 6% by mass or less based on the total mass of the dehydrogenation catalyst.

In the dehydrogenation catalyst of the present aspect, it is preferable that the molar ratio of Sn to Pt (the number of moles of Sn/the number of moles of Pt) be 3 or more, and it is more preferable that the ratio be 6 or more from the viewpoints that side reaction is inhibited, and the reaction efficiency is further improved. It is preferable that the molar ratio of Sn to Pt be 15 or less, and it is more preferable that the ratio be 13 or less, from the viewpoints that excessive covering of Pt particles by Sn is prevented, and the reaction efficiency is increased.

In the dehydrogenation catalyst of the present aspect, it is preferable that the molar ratio of the Group 2 metal element to Al (the number of moles of the Group 2 metal element/the number of moles of Al) be 0.30 or more, and it is more preferable that the ratio be 0.40 or more, from the viewpoints that side reaction is inhibited and the reaction efficiency is further improved. It is preferable that the molar ratio of the Group 2 metal element to Al be 0.60 or less, and it is more preferable that the ratio be 0.55 or less, from the viewpoint that the dispersibility of Pt in a dehydrogenation catalyst is increased.

The contents of Al, the Group 2 metal element, Pt and Sn in the dehydrogenation catalyst can be measured with an inductively coupled plasma-atomic emission spectrometer (ICP-AES) under the following measurement conditions. The dehydrogenation catalyst is subjected to alkali fusion, then converted into an aqueous solution with hydrochloric acid and used for measurement.

Device: manufactured by Hitachi High-Tech Science Corporation, type SPS-3000
High frequency wave output: 1.2 kW
Plasma gas flow rate: 18 L/min
Auxiliary gas flow rate: 0.4 L/min
Nebulizer gas flow rate: 0.4 L/min The dehydrogenation catalyst of the present aspect has pores having a pore size of 6 nm or more and 18 nm or less (a). The dehydrogenation catalyst may have pores having a pore size of 3 nm or less (hereinafter referred to as "pores (b)"), may have pores having a pore size of more than 3 nm and less than 6 nm (hereinafter referred to as "pores (c)"), and may have pores having a pore size of more than 18 nm (hereinafter referred to as "pores (d)").

In the dehydrogenation catalyst of the present aspect, the proportion of the pore volume of the pores (a) may be 60% or more of the total pore volume of the dehydrogenation catalyst. When the proportion of the pore volume of the pores (a) is the above-mentioned proportion or more, side reaction is fully inhibited, and sufficient dehydrogenation activity is obtained. It is preferable that the proportion of the pore volume of the pores (a) be 70% or more of the total pore volume of the dehydrogenation catalyst, and it is further preferable that the proportion be 75% or more. The proportion of the pore volume of the pores (a) may be 90% or less of the total pore volume of the dehydrogenation catalyst. The proportion of the pore volumes of predetermined pores can be calculated by analyzing the results measured at a nitrogen relative pressure of 0 to 0.99 by nitrogen adsorption by the BJH method.

It is preferable that the proportion of the pore volume of the pores (b) be 10% or less of the total pore volume of the dehydrogenation catalyst, and it is more preferable that the proportion be 5% or less. The proportion of the pore volume of the pores (b) may be 1% or more of the total pore volume of the dehydrogenation catalyst.

It is preferable that the proportion of the pore volume of the pores (c) be 15% or less of the total pore volume of a dehydrogenation catalyst, and it is more preferable that the proportion be 10% or less. The proportion of the pore volume of the pores (c) may be 5% or more of the total pore volume of the dehydrogenation catalyst.

It is preferable that the proportion of the pore volume of the pores (d) be 30% or less of the total pore volume of a dehydrogenation catalyst, and it is more preferable that the proportion be 20% or less. The proportion of the pore volume of the pores (d) may be 10% or more of the total pore volume of the dehydrogenation catalyst.

It is preferable that the proportion of the total pore volume of the pores (a) and the pores (c) be 70% or more of the total pore volume of the dehydrogenation catalyst, and it is more preferable that the proportion be 80% or more. The proportion of the total pore volume of the pores (a) and the pores (c) may be 95% or less of the total pore volume of the dehydrogenation catalyst.

The specific surface area of the dehydrogenation catalyst of the present aspect may be the same as that of the below-mentioned carrier.

The carrier may be a metal oxide carrier containing, for example, Al and the Group 2 metal element. The metal oxide carrier may be, for example, a carrier containing alumina ($Al_2O_3$) and an oxide of the Group 2 metal, or may be a composite oxide of Al and the Group 2 metal. The metal oxide carrier may be a carrier containing a composite oxide of Al and a Group 2 metal element and at least one selected from the group consisting of alumina and oxides of Group 2 metal elements. The composite oxide of Al and the Group 2 metal may be, for example, $MgAl_2O_4$.

The content of Al in the carrier may be 20% by mass or more, or may be 30% by mass or more, based on the total mass of the carrier. The content of Al in the carrier may be 70% by mass or less, or may be 60% by mass or less, based on the total mass of the carrier.

The content of the Group 2 metal element in the carrier may be 10% by mass or more, or may be 15% by mass or more, based on the total mass of the carrier. The content of the Group 2 metal element in the carrier may be 30% by mass or less, or may be 20% by mass or less, based on the total mass of the carrier.

The content of the composite oxide of Al and the Group 2 metal element in the carrier may be 60% by mass or more, or may be 80% by mass or more, based on the total mass of the carrier. The content of the composite oxide of Al and the Group 2 metal element in the carrier may be 100% by mass or less, or may be 90% by mass or less based on the total mass of the carrier.

The content of alumina in the carrier may be 10% by mass or more, or may be 30% by mass or more, based on the total mass of the carrier. The content of alumina in the carrier may be 90% by mass or less, and may be 80% by mass or less, based on the total mass of the carrier.

The content of the oxide of the Group 2 metal element in the carrier may be 15% by mass or more, or may be 25% by mass or more, based on the total mass of the carrier. The content of the oxide of the Group 2 metal element in the carrier may be 50% by mass or less, or may be 35% by mass or less, based on the total mass of the carrier.

The carrier may contain another metal element besides Al and the Group 2 metal element. The other metal elements may be at least one selected from the group consisting of, for example, Li, Na, K, Zn, Fe, In, Se, Sb, Ni and Ga. The other metal elements may exist as an oxide, or may exist as a composite oxide with at least one selected from the group consisting of Al and the Group 2 metal element.

The carrier may have pores (a), may have pores (b), may have pores (c), and may have pores (d).

The proportions of the pore volumes of the pores (a), the pores (b), the pores (c) and the pores (d) in the carrier may be, for example, similar to the proportions of the pore volumes of respective pores in the above-mentioned dehydrogenation catalyst. A dehydrogenation catalyst wherein the proportions of pore volumes are in the above-mentioned suitable range is easily obtained thereby.

It is preferable that the acidity of the carrier be nearly neutral from the viewpoint that side reaction is inhibited. Here, the standard of the acidity of a carrier is generally distinguished by the pH measured when the carrier is dispersed in water. That is, the acidity of the carrier can be herein indicated by the pH of a suspension in which the carrier is suspended at 1% by mass. The acidity of the carrier may be preferably pH 5.0 to 9.0, and may be more preferably pH 6.0 to 8.0.

The specific surface area of the carrier may be, for example, 50 $m^2/g$ or more, and it is preferable that the specific surface area be 80 $m^2/g$ or more. The effect of easily increasing the dispersibility of the supported Pt is produced thereby. The specific surface area of the carrier may be, for example, 300 $m^2/g$ or less, and it is preferable that the specific surface area be 200 $m^2/g$ or less. The carrier having such a specific surface area tends not to have micropores which are easily crushed at the time of firing, in which the carrier is exposed to high temperatures. Therefore, the dispersibility of the supported Pt tends to increase easily. The specific surface area of the carrier is measured with a BET specific surface area meter using nitrogen adsorption.

The method for preparing the carrier is not particularly limited, and may be, for example, a sol-gel method, a coprecipitation method, a hydrothermal synthesis method, an impregnation method, a solid phase synthesis method or the like. The impregnation method is preferable from the viewpoint of facilitating adjusting the proportion of the pore volume of the pores (a) to the above-mentioned suitable proportion.

As an example of the method for preparing the carrier, one aspect of the impregnation method will be shown below. First, a carrier precursor containing a second metal element (for example, Al) is added to a solution in which the precursor of a first metal element (for example, a Group 2 metal element) is dissolved, and the solution is stirred. Then, the solvent is removed at reduced pressure, and the obtained solid is dried. The solid after drying is fired to obtain a carrier containing the first metal element and the second metal element. In this aspect, the content of a target metal element contained in the carrier can be adjusted by the concentration of the target metal element in the solution containing the metal element, the amount of the solution used, and the like.

The metal precursor may be, for example, a salt or a complex containing the metal element. The salt containing the metal element may be, for example, an inorganic salt, an organic acid salt, or a hydrate thereof. The inorganic salt may be, for example, a sulfate, a nitrate, a chloride, a phosphate, a carbonate, or the like. The organic salt may be, for example, an acetate, an oxalate, and the like. The complex containing the metal element may be, for example, an alkoxide complex, an ammine complex, or the like.

Examples of the solvent which dissolves the metal precursor include hydrochloric acid, nitric acid, ammonia water, ethanol, chloroform and acetone.

Examples of the carrier precursor containing the second metal element include alumina (for example, γ-alumina). The carrier precursor can be prepared, for example, by a sol-gel method, a coprecipitation method, a hydrothermal synthesis method, or the like. Commercial alumina may be used as the carrier precursor.

The carrier precursor may have the above-mentioned pores (a). The proportion of the pore volume of the pores (a) in the carrier precursor may be 50% or more of the total pore volume of the carrier precursor, may be 60% or more, or may be 70% or more. In this case, adjusting the proportion of the pore volume of the pores (a) in the dehydrogenation catalyst to the above-mentioned suitable proportion is facilitated. The proportion of the pore volume of the pores (a) may be 90% or less. The proportion of the pore volume of predetermined pores in the carrier precursor is measured in a similar manner as the measurement of the proportion of the pore volume of a predetermined pore size in the dehydrogenation catalyst.

Firing can be performed, for example, in the air atmosphere or an oxygen atmosphere. Firing may be performed in one stage or in multiple stages, which are two or more stages. The firing temperature may be a temperature at which the metal precursor can be decomposed, and may be, for example, 200 to 1000° C., or may be 400 to 800° C. When multistage firing is performed, at least one stage thereof may be performed at the above-mentioned firing temperature. The firing temperature in the other stages may be in the same range as the above, or may be 100 to 200° C.

As conditions at the time of stirring, for example, the stirring temperature is 0 to 60° C., and the stirring time is 10 minutes to 24 hours. As conditions at the time of drying, for example, the drying temperature is 100 to 250° C., and the drying time is 3 hours to 24 hours.

The supported metal including Pt and Sn is supported on the dehydrogenation catalyst of the present aspect. The supported metal may be supported on the carrier as an oxide, or may be supported on the carrier as a metal which is a simple substance.

Another metal element except Pt and Sn may be supported on the carrier. Examples of the other metal elements are the same as the examples of the other metal element which the above-mentioned carrier can contain. The other metal elements may be supported on the carrier as a metal which is a simple substance, may be supported as an oxide, or may be supported as a composite oxide with at least one selected from the group consisting of Pt and Sn.

The amount of Pt supported on the carrier is preferably 0.1 parts by mass or more, and more preferably 0.5 parts by mass or more, based on 100 parts by mass of the carrier. The amount of Pt supported on the carrier may be 5 parts by mass or less, or may be 3 parts by mass or less, based on 100 parts by mass of the carrier. In the case of such an amount of Pt, Pt particles formed on the catalyst have a suitable size for dehydrogenation reaction, the platinum surface area per unit platinum weight increases, and a more efficient reaction system can therefore be achieved. In the case of such an amount of Pt, high activity can be maintained over a longer period of time while the catalyst cost is reduced.

The amount of Sn supported on the carrier is preferably 1.5 parts by mass or more, and more preferably 3 parts by mass or more based on 100 parts by mass of the carrier. The amount of Sn supported on the carrier may be 10 parts by mass or less, or may be 8 parts by mass or less based on 100 parts by mass of the carrier. When the amount of Sn is in the above-mentioned range, catalyst deterioration is further suppressed, and high activity tends to be maintained over a longer period of time.

The method for supporting the metal on the carrier is not particularly limited, and examples of the method include a impregnation method, a precipitator method, a coprecipitation method, a kneading method, an ion-exchange method and a pore filling method.

One aspect of the method for supporting metal on a carrier will be shown hereinafter. First, a carrier is added to a solution in which a precursor of a target metal (supported metal) is dissolved in a solvent (for example, an alcohol), and the solution is stirred. Then, the solvent is removed at reduced pressure, and the obtained solid is dried. The solid after drying is fired, and the target metal can be supported on the carrier.

In the above-mentioned supporting method, the precursor of the carrier metal may be a salt or a complex containing the metal element. The salt containing the metal element may be, for example, an inorganic salt, an organic acid salt or a hydrate thereof. The inorganic salt may be, for example, a sulfate, a nitrate, a chloride, a phosphate, a carbonate or the like. The organic salt may be, for example, an acetate, an oxalate or the like. The complex containing the metal element may be, for example, an alkoxide complex, an ammine complex or the like.

As conditions at the time of stirring, for example, the stirring temperature is 0 to 60° C., and the stirring time is 10 minutes to 24 hours. As conditions at the time of drying, for example, the drying temperature is 100 to 250° C., and the drying time is 3 hours to 24 hours.

Firing can be performed, for example, in the air atmosphere or an oxygen atmosphere. Firing may be performed in one stage or in multiple stages, which are two or more stages. The firing temperature may be a temperature at which the precursor of the carrier metal can be decomposed, and may be, for example, 200 to 1000° C., or may be 400 to 800° C. When multistage firing is performed, at least one stage thereof may be performed at the above-mentioned firing temperature. The firing temperature in the other stages may be in the same range as the above, or may be 100 to 200° C.

The degree of dispersion of Pt in the dehydrogenation catalyst of the present aspect may be 10% or more, or may be preferably 15% or more. According to the dehydrogenation catalyst having such a degree of dispersion of Pt, side reaction is further inhibited, and high activity tends to be maintained over a longer period of time. The degree of dispersion of Pt is measured by a method for measuring the degree of dispersion of metal using CO as an adsorption species with the following device and under the following measurement conditions.

Device: Degree of dispersion of metal measuring device R-6011 manufactured by Ohkurariken Co., Ltd.

Gas flow rate: 30 mL/minute (helium, hydrogen)

Amount of Sample: Around 0.1 g (weighed precisely to the fourth decimal place)

Pretreatment: The temperature is raised to 400° C. in a hydrogen air flow over 1 hour, and reduction treatment is performed at 400° C. for 60 minutes. Then, gas is switched from hydrogen to helium, purging is performed at 400° C. for 30 minutes, and cooling is performed to room temperature in a helium air flow. The detector is left to stand at room temperature until the detector becomes stable, and a CO pulse is then performed.

Measurement conditions: First, 0.0929 $cm^3$ of carbon monoxide is pulse-injected every time with helium at normal pressure circulated at room temperature (27° C.), and the amount of adsorption is measured. The number of times of adsorption is performed until the adsorption is saturated (at least 3 times, at most 15 times). The degree of dispersion is calculated from the measured amount of adsorption.

As long as the dehydrogenation catalyst is a catalyst containing Pt, the dehydrogenation catalyst may be a dehydrogenation catalyst other than the above. Although, for example, a dehydrogenation catalyst containing Cr as an active metal is known as a dehydrogenation catalyst, the above-mentioned effect in the presence of water is not obtained with such a dehydrogenation catalyst.

The dehydrogenation catalyst may be molded by a method such as an extrusion method or a tablet compression method.

Unless the physical properties or the catalyst performance of a catalyst are deteriorated, the dehydrogenation catalyst may contain a molding auxiliary from the viewpoint of improving moldability in a molding step. The molding auxiliary may be at least one selected from the group consisting of, for example, a thickener, a surfactant, a water retention agent, a plasticizer, a binder material, and the like. The molding step of molding a dehydrogenation catalyst may be performed in a suitable stage of the production process of the dehydrogenation catalyst in view of the reactivity of the molding auxiliary.

The shape of the molded dehydrogenation catalyst is not particularly limited, and the shape can be suitably selected depending on the form in which the catalyst is used. For example, the shape of the dehydrogenation catalyst may be a shape such as a pellet shape, a granular shape, a honeycomb shape or a sponge shape.

A dehydrogenation catalyst subjected to reduction treatment as a pretreatment may be used. The reduction treatment can be performed by maintaining the dehydrogenation catalyst, for example, in a reducing gas atmosphere at 40 to 600° C. The retention time may be, for example, 0.05 to 24 hours. The reducing gas may be, for example, hydrogen, carbon monoxide or the like.

The use of the dehydrogenation catalyst subjected to reduction treatment enables to shorten an induction period in an early stage of dehydrogenation reaction. The induction period in an early stage of reaction means a state in which the activity of the catalyst is low because, out of active metal contained in the catalyst, active metal which is reduced to be in an activated state is very little.

Subsequently, reaction conditions in the cyclization step and the like will be described in detail.

The cyclization step is a step of reacting the second raw material with the dehydrogenation catalyst in the presence of water and performing the cyclodehydrogenation reaction of the C8 components to obtain p-xylene.

The cyclization step may be performed, for example, using a reactor filled with the dehydrogenation catalyst by circulating the second raw materials and water in the reactor. Various reactors used for gaseous phase reaction with solid catalysts can be used as the reactor. Examples of the reactor include a fixed bed reactor, a radial flow reactor and a tubular reactor.

The reaction style of cyclodehydrogenation reaction may be, for example, a fixed bed style, a movable bed style or a fluidized bed style. Among these, the fixed bed style is preferable from the viewpoint of facility cost.

It is preferable that the amount of water be 0.1 equivalents or more, and it is more preferable that the amount be 0.5 equivalents or more based on the C8 components in the second raw material. Monomerization which is a side reaction is inhibited still more remarkably thereby, and para-xylene can be produced more efficiently. It is preferable that the amount of water be 10 equivalents or less, and it is more preferable that the amount be 5 equivalents or less based on the C8 components in the second raw material. The drainage amount can be reduced thereby.

In a cyclization step, cyclodehydrogenation reaction may be performed in the presence of hydrogen (namely, in the presence of water and hydrogen). In this case, the second raw material, water, and hydrogen are circulated in the reactor.

It is preferable that the amount of hydrogen be 0.1 equivalents or more, and it is more preferable that the amount be 0.3 equivalents or more based on the C8 components in the second raw material. The yield of para-xylene tends to be improved further thereby. It is preferable that the amount of hydrogen be 10 equivalents or less, and it is more preferable that the amount be 5 equivalents or less based on the C8 components in the second raw material. The yield of para-xylene tends to be improved further thereby.

The reaction temperature of cyclodehydrogenation reaction, namely, the temperature in the reactor, may be 300 to 800° C., may be 400 to 700° C., or may be 500 to 650° C., from the viewpoint of reaction efficiency. If the reaction temperature is 300° C. or more, the amount of p-xylene generated tends to increase further. If the reaction temperature is 800° C. or less, the coking speed is not too high, and high activity of the dehydrogenation catalyst therefore tends to be maintained over a longer period of time.

The reaction pressure, namely, the atmospheric pressure in the reactor, may be 0.01 to 1 MPa, may be 0.05 to 0.8 MPa, and may be 0.1 to 0.5 MPa. If the reaction pressure is in the above-mentioned range, dehydrogenation reaction proceeds easily, and still more excellent reaction efficiency tends to be obtained.

When the cyclization step is performed in a continuous reaction style in which the second raw material is fed continuously, the weight hourly space velocity (hereinafter referred to as "WHSV"), for example, may be $0.1\ h^{-1}$ or more, or may be $0.5\ h^{-1}$ or more. The WHSV may be $20\ h^{-1}$ or less, or may be $10\ h^{-1}$ or less. Here, the WHSV is the ratio of the speed of raw material gas (the second raw material) fed (fed amount/time) F to the mass of the dehydrogenation catalyst W (F/W). When the WHSV is $0.1\ h^{-1}$ or more, the reactor size can be further reduced. When the WHSV is $20\ h^{-1}$ or less, the rate of the C8 components converted can be further increased. Further preferable ranges of the amounts of the raw material gas and the catalyst used may be selected optionally depending on reaction conditions, the activity of the catalyst and the like, and the WHSV is not limited to the above-mentioned range.

(Collection Step)

In the collection step, p-xylene is collected from the reaction product obtained in the cyclization step.

The collection means is not particularly limited, and well-known collection means can be adopted. Examples of the collection means include crystallization.

In the collection step, the C4 collected fraction containing at least one selected from the group consisting of isobutene and isobutane can be further collected from the reaction product. The yield of p-xylene can be increased by collecting isobutene in the reaction product and recycling the isobutene for a raw material of the dimerization step. When isobutane in the reaction product is collected and recycled as the raw material of the dimerization step or the cyclization step, isobutane is converted into isobutene with the dehydrogenation catalyst in the cyclization step. The yield of p-xylene can be further increased by further recycling isobutene derived from isobutane for the raw material of the dimerization step.

Since isobutene and isobutane have similar boiling points, it is difficult to separate and collect these individually. For this reason, when the reaction product contains isobutene and isobutane, it is preferable to collect a mixture of isobutene and isobutane as the C4 collected fraction in the collection step. At this time, it is preferable to recycle the collected C4 collected fraction for the dimerization step.

In the collection step, the C8 collected fraction containing at least one selected from the group consisting of diisobutylene, 2,2,4-trimethylpentane, 2,5-dimethylhexane, 2,5-dimethylhexene and 2,5-dimethylhexadiene can also be further collected from the reaction product. The recycle of the C8 collected fraction as the second raw material of the cyclization step enables to further increase the yield of p-xylene.

At the present embodiment, performing the cyclization step in the presence of water inhibits the monomerization in the cyclization step and increases the rate of the C8 components in the reaction product. The recycle of the C8 components for the cyclization step enables to contribute to improvement in the yield of p-xylene. For this reason, according to the production method according to the present embodiment, p-xylene can be obtained from a raw material containing isobutene at high process efficiency.

EXAMPLES

Hereinafter, the present invention will be described by Examples more specifically; however, the present invention is not limited to Examples.

Example 1

<Preparation of Catalyst A>

As a carrier precursor, 6.0 g of γ-alumina classified at 0.5 to 1 mm (Neobead GB-13, manufactured by MIZUSAWA INDUSTRIAL CHEMICALS, LTD., the pH of a suspension in which the γ-alumina is suspended in water at a concentration of 1% by mass: 7.9) was provided. The carrier precursor and a solution in which 15.1 g of $Mg(NO_3)_2 \cdot 6H_2O$ is dissolved in 45 mL of water were mixed. The obtained mixed liquid was stirred at 40° C. and 0.015 MPa for 30 minutes using a rotary evaporator and then further stirred at 40° C., normal temperature for 30 minutes. Then, water was removed at reduced pressure with stirring the mixed liquid. The obtained solid was dried in an oven at 130° C. overnight. Next, the solid after drying was fired with air circulated in two stages which are at 550° C. for 3 hours and at 800° C. for 3 hours to obtain a carrier A containing $MgAl_2O_4$.

Platinum was impregnated and supported on 10.0 g of the carrier A using a solution of dinitrodiammine platinum (II) in nitric acid (manufactured by Tanaka Kikinzoku Kogyo K.K., $[Pt(NH_3)_2(NO_2)_2]/HNO_3$) so that the amount of platinum supported was around 1% by mass, the resultant was dried at 130° C. overnight, and then fired at 550° C. for 3 hours. Subsequently, the carrier A supporting platinum was mixed with an aqueous solution in which 0.82 g of sodium stannate (manufactured by Showa Kako Corporation, $Na_2SnO_2 \cdot 3H_2O$) was dissolved in around 30 ml of water, and water was removed at around 50° C. with the evaporator. Then, the resultant was dried at 130° C. overnight, and then fired at 550° C. for 3 hours to obtain a catalyst A. When the obtained catalyst A was analyzed by the ICP method, the amount of Pt supported was 0.92% by mass, and the amount of Sn supported was 3.0% by mass.

<Production of p-Xylene>

A C4 fraction obtained by treating Middle East crude oil with a fluidized catalytic cracker was fractionated with a reactive distillation device, isobutane and isobutene were obtained from the overhead, normal butane and normal butene were obtained from the bottom. The isobutane in overhead gas was 76% by mass, and the isobutene was 24% by mass. This overhead gas was treated with Amberlyst 35, which is a strongly acidic ion-exchange resin, using a fixed bed flow type reactor under the conditions of 120° C., normal pressure and WHSV=50 $h^{-1}$ to obtain a product of 76% by mass of isobutane, 23% by mass of 2,4,4-trimethylpentene, and 1% by mass of others (a first product).

Subsequently, cyclodehydrogenation reaction was performed with the fixed bed flow type reactor under the conditions of 550° C., normal pressure and WHSV=1 $h^{-1}$ at 3 equivalents of water and 1 equivalent of nitrogen based on 1 equivalent of diisobutylene using the first product as a raw material. The catalyst A was used for a catalyst. A reaction product from 1 hour after to 2 hours after the reaction start, a reaction product from 2 hours after to 3 hours after, a reaction product from 3 hours after to 4 hours after, and a reaction product from 4 hours after to 5 hours after were collected and analyzed separately. The results are shown in Table 1. In Table 1, the C4 collected fraction indicates the total amount of isobutane and isobutene, and the C8 collected fraction indicates the total amount of diisobutylene, 2,2,4-trimethylpentane, 2,5-dimethylhexane, 2,5-dimethylhexene, and 2,5-dimethylhexadiene.

Example 2 p-Xylene was produced in the same manner as in Example 1 except that "3 equivalents of water and 1 equivalent of nitrogen" in the cyclodehydrogenation reaction were changed to 3 equivalents of water, 0.7 equivalents of hydrogen, and 0.3 equivalents of nitrogen. The results are shown in Table 2.

Comparative Example 1 p-Xylene was produced in the same manner as in Example 1 except that "3 equivalents of water and 1 equivalent of nitrogen" in the cyclodehydrogenation reaction were changed to 2 equivalents of nitrogen. The results are shown in Table 3.

Example 3 p-Xylene was produced in the same manner as in Example 1 except that the reaction temperature in the cyclodehydrogenation reaction was changed from 550° C. to 500° C. The results are shown in Table 4.

Comparative Example 2 p-Xylene was produced in the same manner as in Example 3 except that "3 equivalents of water and 1 equivalent of nitrogen" in the cyclodehydrogenation reaction were changed to 4 equivalents of nitrogen. The results are shown in Table 5.

Reference Example 1

<Preparation of Catalyst B>

The Carrier A was prepared by the same method as in Example 1. Subsequently, 10.0 g of the carrier A was subjected to impregnation and supporting using an aqueous solution of chromium nitrate (manufactured by Wako Pure Chemical Industries, Ltd., $[Cr(NO_3)_2]6H_2O$) and $Mg(NO_3)_2 \cdot 6H_2O$ so that the amount of chromium supported was around 13% by mass in terms of a carrier weight ratio, the amount of magnesium supported was 1.5% by mass in terms of a carrier weight ratio, the resultant was dried at 110° C. overnight, and then fired at 600° C. for 4 hours to obtain a catalyst B.

<Production of p-Xylene> p-Xylene was produced in the same manner as in Example 1 except that the catalyst B was used instead of the catalyst A, "3 equivalents of water and 1 equivalent of nitrogen" in the cyclodehydrogenation reaction were changed to 1 equivalent of water and 1 equivalent of nitrogen, the reaction temperature of the cyclodehydrogenation reaction was changed from 550° C. to 500° C. The results are shown in Table 6.

Reference Example 2 p-Xylene was produced in the same manner as in Reference Example 1 except that "1 equivalent of water and 1 equivalent of nitrogen" in the cyclodehydrogenation reaction were changed to 2 equivalents of nitrogen. The results are shown in Table 7.

TABLE 1

| | Example 1 | | | |
|---|---|---|---|---|
| | 1 to 2 hours after | 2 to 3 hours after | 3 to 4 hours after | 4 to 5 hours after |
| p-Xylene | 15.30 | 10.15 | 9.00 | 8.06 |
| C4 COLLECTED FRACTION | 29.57 | 39.42 | 42.74 | 45.47 |
| C8 COLLECTED FRACTION | 46.55 | 42.37 | 40.57 | 39.12 |

(% by mass)

TABLE 2

| | Example 2 | | | |
|---|---|---|---|---|
| | 1 to 2 hours after | 2 to 3 hours after | 3 to 4 hours after | 4 to 5 hours after |
| p-Xylene | 21.32 | 16.47 | 12.97 | 10.88 |
| C4 COLLECTED FRACTION | 34.93 | 38.44 | 42.79 | 44.49 |
| C8 COLLECTED FRACTION | 35.26 | 37.12 | 36.68 | 37.08 |

(% by mass)

TABLE 3

| | Comparative Example 1 | | | |
|---|---|---|---|---|
| | 1 to 2 hours after | 2 to 3 hours after | 3 to 4 hours after | 4 to 5 hours after |
| p-Xylene | 22.79 | 13.52 | 8.13 | 5.83 |
| C4 COLLECTED FRACTION | 57.76 | 65.31 | 70.80 | 74.02 |
| C8 COLLECTED FRACTION | 9.43 | 11.61 | 11.75 | 11.26 |

(% by mass)

TABLE 4

| | Example 3 | | | |
|---|---|---|---|---|
| | 1 to 2 hours after | 2 to 3 hours after | 3 to 4 hours after | 4 to 5 hours after |
| p-Xylene | 8.43 | 6.69 | 5.46 | 4.57 |
| C4 COLLECTED FRACTION | 7.54 | 10.08 | 11.81 | 12.70 |

TABLE 4-continued

| | Example 3 | | | |
|---|---|---|---|---|
| | 1 to 2 hours after | 2 to 3 hours after | 3 to 4 hours after | 4 to 5 hours after |
| C8 COLLECTED FRACTION | 81.17 | 80.55 | 80.01 | 80.13 |

(% by mass)

TABLE 5

| | Comparative Example 2 | | | |
|---|---|---|---|---|
| | 1 to 2 hours after | 2 to 3 hours after | 3 to 4 hours after | 4 to 5 hours after |
| p-Xylene | 7.81 | 6.20 | 4.93 | 4.23 |
| C4 COLLECTED FRACTION | 17.06 | 16.72 | 18.43 | 19.39 |
| C8 COLLECTED FRACTION | 71.43 | 73.66 | 73.78 | 73.75 |

(% by mass)

In Examples 1 and 2, the generation of the C4 collected fraction by monomerizing is inhibited as compared with Comparative Example 1, and a large amount of the C8 collected fraction is collected. As is clear from comparison with Example 3 and Comparative Example 2, even when the reaction temperature is 500° C., and the conversion rate is reduced, the generation of the C4 collected fraction by monomerizing is inhibited due to the existence of water.

TABLE 6

| | Reference Example 1 | | | |
|---|---|---|---|---|
| | 1 to 2 hours after | 2 to 3 hours after | 3 to 4 hours after | 4 to 5 hours after |
| p-Xylene | 7.93 | 5.71 | 5.79 | 7.22 |
| C4 COLLECTED FRACTION | 35.95 | 35.96 | 36.16 | 35.85 |
| C8 COLLECTED FRACTION | 47.11 | 51.17 | 52.48 | 52.36 |

(% by mass)

TABLE 7

| | Reference Example 2 | | | |
|---|---|---|---|---|
| | 1 to 2 hours after | 2 to 3 hours after | 3 to 4 hours after | 4 to 5 hours after |
| p-Xylene | 14.81 | 12.67 | 11.35 | 10.07 |
| C4 COLLECTED FRACTION | 32.51 | 33.74 | 35.26 | 36.57 |
| C8 COLLECTED FRACTION | 44.62 | 46.82 | 47.88 | 48.73 |

(% by mass)

As shown in Reference Example 1 and Reference Example 2, even though water coexists in the reaction system, monomerization could not be inhibited in the case where the Cr catalyst was used.

INDUSTRIAL APPLICABILITY

According to the present invention, a method for producing p-xylene which enables to obtain p-xylene from C4 components containing isobutene as raw materials at a high process efficiency can be provided.

The invention claimed is:

1. A method for producing p-xylene, comprising:
bringing a first raw material comprising isobutene into contact with a dimerization catalyst to generate C8 components comprising diisobutylene;
bringing a second raw material comprising the C8 components into contact with a dehydrogenation catalyst comprising Pt in the presence of water to obtain a reaction product comprising p-xylene, wherein the amount of water is from 0.1 equivalents to 10 equivalents based on the C8 components in the second raw material; and
collecting p-xylene from the reaction product.

2. The method according to claim 1, wherein a C8 collected fraction comprising at least one selected from the group consisting of diisobutylene, 2,2,4-trimethylpentane, 2,5-dimethylhexane, 2,5-dimethylhexene and 2,5-dimethylhexadiene is further collected from the reaction product.

3. The method according to claim 2, wherein the C8 collected fraction is recycled to the second raw material.

4. The method according to claim 1, wherein a C4 collected fraction comprising at least one selected from the group consisting of isobutene and isobutane is further collected from the reaction product.

5. The method according to claim 4, wherein the C4 collected fraction is recycled to the first raw material.

6. The method according to claim 1, wherein the dimerization catalyst comprises at least one acidic catalyst selected from the group consisting of sulfuric acid, zeolite, solid phosphoric acid, hydrofluoric acid, ionic liquids, and ion-exchange resins.

7. The method according to claim 1, wherein the dehydrogenation catalyst further comprises Sn.

* * * * *